United States Patent [19]

Romine et al.

[11] Patent Number: 5,015,369

[45] Date of Patent: May 14, 1991

[54] ASSEMBLY FOR FILTERING AMNIOTIC FLUID

[76] Inventors: Lori Romine, 11735 SW. 112th Ter., Miami, Fla. 33186; Ronald Sholders, 7640 SW. 168th St., Miami, Fla. 33157; Richard Warren, c/o 11735 SW. 112 Ter., Miami, Fla. 33186

[21] Appl. No.: 468,207

[22] Filed: Jan. 22, 1990

[51] Int. Cl.⁵ .............................................. B01D 35/02
[52] U.S. Cl. .............................. 210/136; 210/416.1; 210/418; 210/435; 210/446; 210/448; 604/27; 604/31
[58] Field of Search ..................... 604/4.5, 27, 31, 190, 604/317, 406; 210/136, 416.1, 418, 435, 446, 448, 443

[56] References Cited

U.S. PATENT DOCUMENTS

| | | | |
|---|---|---|---|
| 3,520,416 | 7/1970 | Keedwell | 210/508 |
| 3,892,226 | 7/1975 | Rosen | 604/190 |
| 4,100,923 | 7/1978 | Southern | 604/31 |
| 4,170,056 | 10/1979 | Meyst et al. | 210/446 |
| 4,229,306 | 10/1980 | Hein et al. | 210/446 |
| 4,310,017 | 1/1982 | Raines | 604/31 |
| 4,447,226 | 5/1984 | Mayoral | 604/31 |
| 4,685,472 | 8/1987 | Muto | 210/446 |
| 4,817,599 | 4/1989 | Drews | 604/27 |
| 4,820,261 | 4/1989 | Schmoll et al. | 604/4 |
| 4,957,629 | 9/1990 | Smith et al. | 210/443 |

Primary Examiner—W. Gary Jones
Attorney, Agent, or Firm—Malloy, Downey & Malloy

[57] ABSTRACT

An assembly for the removal and examination of amnioytes in early pregnancy by filtering the amniotic fluid and returning the fluid to the fetus subsequent to filtering wherein a conduit structure has a filter incorporated therein and is constructed to include two different paths of fluid flow, one for drawing off said amniotic fluid through the filter means and one for returning the amniotic fluid subsequent to filtering along a path which bypasses said filter structure.

14 Claims, 1 Drawing Sheet

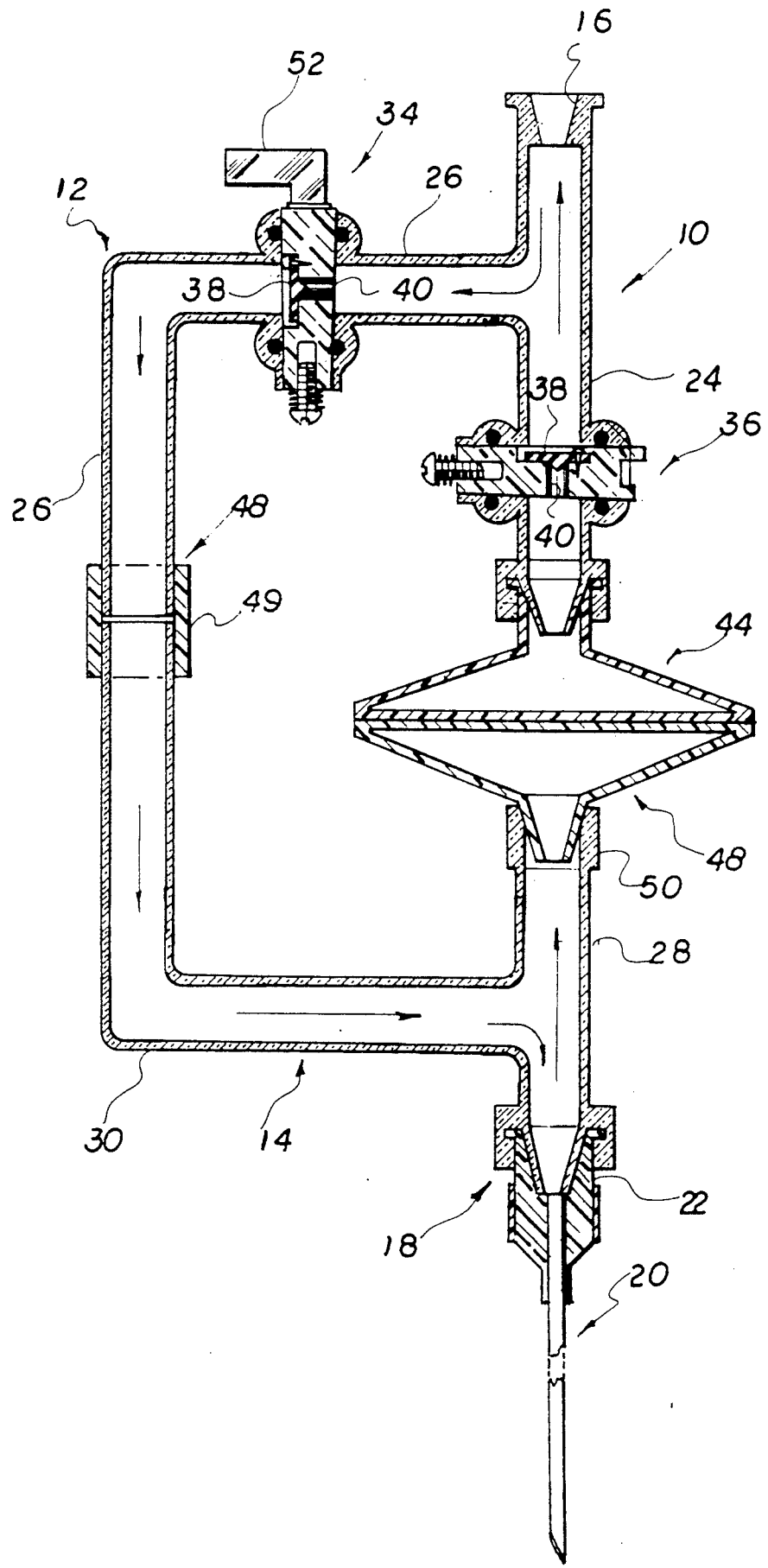

ASSEMBLY FOR FILTERING AMNIOTIC FLUID

BACKGROUND OF THE INVENTION

1. Field of the Invention

A conduit structure used in combination with a syringe and a penetrating needle for the withdrawing, filtering and subsequent return of amniotic fluid of a fetus during pregnancy for the purpose of examination of amniocytes.

2. Description of the Prior Art

The testing of amniotic fluid, especially during the early stages of pregnancy, has been conducted and recognized for some time as being an accurate method of determining irregularities and/or general health and well-being of the fetus. Typically, in the testing of such amniotic fluid, the fluid is withdrawn directly from the fetal sac by means of an elongated needle attached to a syringe instrument. The removed fluid is then submitted to other procedures and apparatus for laboratory testing. Based on the popularity and success of such techniques, it has become desired in the medical profession to have a more efficient means of withdrawing, filtering and subsequently returning the amniotic fluid to the fetus by means of a close system specifically wherein a preferred structure would incorporate a filter mechanism capable of filtering out the amniocytes from the amniotic fluid subsequent to returning of the fluid to the fetus. Naturally, such an apparatus including the aforementioned filter structure should be defined as a closed system in order to maintain a sterile environment.

Other apparatus exists in the medical profession which incorporate certain basic structural features such as a withdrawing syringe, a penetrating needle and some type of filter apparatus. Typically, such structures are utilized in the area of blood sampling and collection. The following U.S. Patents are generally representative of known prior art structures of the type set forth above but which are not related to the removal, sampling and return of amniotic fluid to and from the fetus: U.S. Pat. Nos. 3,520,416; 3,892,226; and 4,685,472.

While the structures disclosed in the above-noted patents are assume to be operable for their intended function, there are not specifically adapted for the removal, filtering and/or testing and subsequent return of amniotic fluid from the fetus.

SUMMARY OF THE INVENTION

The present invention relates to an assembly for the removal, filtering and replacement of amniotic fluid from the fetus especially during early stages of pregnancy. The subject filtering assembly comprises a first and second conduit structures, each having separate conduit segments. The first and second conduit sections are removably attached to one another and both are attached to a filtering means. The separate conduit segments, being removably interconnected to one another, of the separate conduit sections serves to define separate flow paths of the amniotic fluid as it enters the subject assembly and, subsequent to filtering, as it is returned to the fetus. A filtering means is incorporated in interconnection between what may be defined as a first flow path. A first conduit section has an open end to which a syringe may be attached. The second conduit section also includes an open end to which a penetrating needle may be attached. Opposite ends of the conduit sections, defined by the aforementioned separate conduit segments, are removably attached to one another. The filter structure is disposed within a first path of fluid flow extending between the needle structure through the filter means and to the syringe.

Valve means are incorporated in flow regulating relation in both a first and second path of fluid flow. Manipulation of the valve means between a flow-on and flow-off position serves to regulate fluid flow and allow alternate withdrawal of fluid from the fetus through the filter apparatus and, subsequent to filter, return of the amniotic fluid along the second path of fluid flow which is specifically designed to bypass the filter means associated with the subject invention.

Amniotic fluid is filtered upon withdrawal thereof and passed through the filter structure and subsequently returned to the fetus by alternately filling and emptying the syringe while maintaining the aforementioned valve means in the appropriate position. Once the above-noted procedure has been accomplished, a needle cover is placed over the penetrating needle and the entire system, including the filter mechanism, is given to laboratory or testing personnel. The valve means is again re-positioned and the second conduit section is removed from both the filter means and the first conduit section. Such second conduit section, including the penetrating needle may thereafter be discarded. Cell culture media in a syringe can then be backwashed through the filter to harvest the amniocytes maintained in the filter.

BRIEF DESCRIPTION OF THE DRAWINGS

The single FIGURE comprises a longitudinal sectional view of the filtering apparatus of the present invention including directions of fluid flow therethrough.

Like reference numerals refer to like parts throughout the several views of the drawing.

DETAILED DESCRIPTION OF THE PREFERRED EMBODIMENT

As shown in the accompanying drawing, the subject invention relates to a filtering assembly generally indicated as 10 for the removal, filtering and return of amniotic fluid for purposes of diagnostic testing. The assembly 10 comprises a first conduit section generally indicated as 12 and a second conduit section generally indicated as 14. The first conduit section includes an open end as at 16 designed to be connected to a substantially conventional syringe structure such that fluid may be drawn into and forced out of the syringe through conventional operation thereof. Similarly, the second conduit section includes a generally open end as at 18 designed to have a penetrating needle or like assembly attached thereto as at 20 by what may be considered a conventional needle mount type structure 22. The needle 20 is used for penetration of the patient in the area of the fetus for purposes of communicating directly with the amniotic fluid. The first conduit section 12 comprises a first conduit segment 24 and a second conduit segment 26 being substantially separated from the first conduit segment 24 Both the first and second conduit segments 24 and 26 are disposed in fluid communication with the open end 16 and a syringe structure attached thereto.

Similarly, the second conduit section 14 includes a first conduit segment 28 and a second conduit segment 30, both disposed in fluid communication with the open end 18 and the needle structure 20.

Other structural features of the present invention include the existence of a valve means including a first valve structure generally indicated as 34 and a second valve structure generally indicated as 36. Both valve structures 34 and 36 are selectively positionable between a flow-on and a flow-off position. It is also important to note that both valve structures 34 and 36 are structured to operate essentially as one-way check valves due to the existence of a flap valve member 38 disposed in fluid regulating relation to a valve opening and seat structure 40. Naturally, other structures could be incorporated in each of the valves 34 and 36 in order to render them functional as a one-way check valve.

The filter means generally indicated as 44 may comprises any type of multi-pore or similar filter structure and is similarly interconnected between the first conduit segment 24 of the first conduit section 12 and the first conduit segment 28 of the second conduit section 14. Interconnection between the first and second conduit sections 12 and 14 is such that the first conduit segments of each conduit section are connected in fluid communication with one another through the filter means 44 to define a first path of fluid flow. Similarly, a second path of fluid flow may be defined by interconnected fluid communicating second conduit segments 26 and 30 of the first and second conduit sections 12 and 14 respectively. The connections of the respective segments occur at a correspondingly positioned connecting junction as at 46 and 48 through the use of substantially conventional conduit connectors as at 49 and 50.

In operation, a first valve structure 34 is turned to a flow-off position approximately 90° to that shown in the accompanying FIGURE by manipulation of a handle, knob or the like 52. The syringe, attached to the open end 16, is then manipulated to withdraw fluid through the needle structure 20, the first conduit segment 28 of the second conduit section 14, the filter means 44, the valve structure 36 (positioned in a flow-on position) and the first conduit segment 24 of the first conduit section 12. Air is cleared from the system by virtue of the withdrawal of the amniotic fluid in the manner set forth herein.

Valve one is then turned to its flow-on position as shown in the accompanying FIGURE again through selective manipulation of the knob or handle 52. The second valve structure 36 remains in the position shown in the accompanying FIGURE. Because the second valve structure 36 is a one-way check valve, the existing valve member 38 will remain closed. Compression of the syringe attached to the open end 16 so as to force fluid therefrom will therefore be prevented from traveling back through the first path of fluid flow and through the filter 44, but instead will pass along the second path of fluid flow defined by the first conduit segment 26, valve structure 34 and second valve conduit 30 of the second conduit section 14. It will then flow back through the needle structure 20 so as to return the amniotic fluid, subsequent to filtration, back to the fetus.

Fluid is filtered upon withdrawal and return thereof to the fetus by alternately filling and emptying the syringe while the first and second valve structures 34 and 36 are maintained in the position shown in the accompanying FIGURE. Such alternating direction of fluid flow between the first and second flow paths, as defined above, is accomplished in that the valve structures 34 and 36 operate as check valves in the flow-on position as shown in the accompanying FIGURE.

Subsequently, a cover is replaced onto the needle structure 20 for protection of medical personnel and the entire system is given to the laboratory. The laboratory personnel manipulates the valve structure 36 approximately 180° to reverse the regulated flow of the check valve. In such a position, the check valve associated with the valve structure 36 will allow fluid flow only from the open end 16 and the syringe thereto back through the filter means 44 so as to effectively backwash the filter. Cell culture media in a syringe can now be backwashed through the filter to harvest the amniocytes.

Now that the invention has been described, What is claimed is:

1. A filtering assembly for removing amniocytes from amniotic fluid during pregnancy, said assembly comprising:
   (a) a conduit structure including a first conduit section having one open end structured for connection to a syringe and having separate conduit segments both disposed in fluid communication with said open end,
   (b) said conduit structure further including a second conduit section removably connected to said first conduit section and including two conduit segments connected to said first conduit section,
   (c) said second conduit section including an open end structured for connection to a needle positioned and structured to allow fluid flow therethrough into and out of said conduit structure,
   (d) filter means connected in fluid communication between said first and second conduit sections for filtering out amniocytes, for examination, from said amniotic fluid,
   (e) said first and second conduit sections structured to define different paths of fluid flow between the syringe and the needle and into and out of said needle structure,
   (f) valve means mounted on said conduit structure in flow regulating relation along said different paths of fluid flow between the syringe and the needle, and
   (g) said filter means disposed in flow receiving relation along one of said different flow paths from the needle to syringe.

2. An assembly as in claim 1 wherein said first and second conduit sections are removably connected to one another, said filter means detachable from said second conduit section and maintained in attached relation to said first conduit section.

3. An assembly as in claim 2 wherein said valve means is mounted on said first conduit section and selectively positionable between a flow-on and a flow-off position.

4. An assembly as in claim 3 wherein said valve means comprises a plurality of valve structures, each mounted in flow regulating relation along a different one of said paths of fluid flow.

5. An assembly as in claim 4 wherein said valve means is structured to establish fluid flow along a first path of fluid flow defined from the needle to the syringe and through said filter means.

6. An assembly as in claim 5 wherein said valve means is structured and positionable to direct fluid flow along said first path of fluid flow from the needle, through said filter means to said syringe and subsequently, along a second path of fluid flow defined from the syringe to the needle in bypassing relation to said filter means.

7. An assembly as in claim 1 wherein said first and second conduit sections each include a first segment connected in fluid communication with one another and defining a first path of fluid flow between the needle and the syringe through said filter means.

8. An assembly as in claim 7 wherein said first and second conduit sections each include a second segment connected in fluid communication with one another and defining a second path of fluid flow between the syringe and the needle in bypassing relation to the filter means.

9. An assembly as in claim 8 wherein said valve means comprises a first valve structure mounted in fluid regulating relation to said first path of fluid flow and a second valve structure mounted in fluid regulating relation to said second path of fluid flow.

10. An assembly as in claim 9 wherein each of said valve structures is positionable between a flow-on and a flow-off position and wherein each of said valve structures is constructed as a one-way check valve when in said flow-on position.

11. An assembly as in claim 10 wherein each of said valve structures is disposed in a flow-on position and said check valve thereof structured to direct fluid flow along said first path upon fluid drawn from the needle to the syringe by the syringe.

12. An assembly as in claim 11 wherein each of said valve structures is disposed in said open position and said check valve thereof being structured to direct fluid flow along said second path of fluid flow.

13. An assembly as in claim 9 further comprising a third path of fluid flow defined by said first valve disposed to force fluid flow of culture media through said filter means, whereby said filter means is backwashed.

14. An assembly as in claim 8 wherein said first and second conduit sections are removably attachable to one another at connecting junctions of said first and second conduit segments of each of said first and second conduit sections.

* * * * *